(12) United States Patent
Bartorelli et al.

(10) Patent No.: US 9,555,084 B2
(45) Date of Patent: *Jan. 31, 2017

(54) COMBINATION OF GROWTH FACTORS, CYTOKINES, ANTIBACTERIAL/ANTIVIRAL FACTORS, STEM CELL STIMULATING FACTORS, COMPLEMENT PROTEINS C3A/C4A, IMMUNOGLOBULINS AND CHEMOTACTIC FACTORS

(71) Applicant: INNOMED S.A., Luxembourg (LU)

(72) Inventors: Alberto Bartorelli, Crans sur Sierre (CH); Maria Rosa Gobbi, Fino Mornasco (IT)

(73) Assignee: INNOMED S.A., Luxembourgh (LU)

( * ) Notice: Subject to any disclaimer, the term of this patent is extended or adjusted under 35 U.S.C. 154(b) by 0 days.

This patent is subject to a terminal disclaimer.

(21) Appl. No.: 14/369,127

(22) PCT Filed: Dec. 27, 2012

(86) PCT No.: PCT/EP2012/076962
§ 371 (c)(1),
(2) Date: Jun. 26, 2014

(87) PCT Pub. No.: WO2013/098333
PCT Pub. Date: Jul. 4, 2013

(65) Prior Publication Data
US 2014/0369957 A1    Dec. 18, 2014

(30) Foreign Application Priority Data

| Dec. 30, 2011 | (IT) | MI2011A2432 |
|---|---|---|
| Dec. 30, 2011 | (IT) | MI2011A2433 |
| Dec. 30, 2011 | (IT) | MI2011A2435 |
| Dec. 30, 2011 | (IT) | MI2011A2439 |
| Dec. 30, 2011 | (IT) | MI2011A2440 |
| Dec. 30, 2011 | (IT) | MI2011A2441 |
| Dec. 30, 2011 | (IT) | MI2011A2443 |
| Dec. 30, 2011 | (IT) | MI2011A2445 |
| Dec. 30, 2011 | (IT) | MI2011A2446 |

(51) Int. Cl.
| A61K 38/18 | (2006.01) |
| A61K 38/19 | (2006.01) |
| A61K 38/20 | (2006.01) |
| A61K 38/00 | (2006.01) |
| A61K 38/47 | (2006.01) |
| A61K 35/16 | (2015.01) |
| A61K 35/20 | (2006.01) |
| A61K 35/50 | (2015.01) |
| A61K 38/21 | (2006.01) |
| A61K 39/395 | (2006.01) |

(52) U.S. Cl.
CPC ............ *A61K 38/47* (2013.01); *A61K 35/16* (2013.01); *A61K 35/20* (2013.01); *A61K 35/50* (2013.01); *A61K 38/1825* (2013.01); *A61K 38/1841* (2013.01); *A61K 38/1875* (2013.01); *A61K 38/191* (2013.01); *A61K 38/2006* (2013.01); *A61K 38/217* (2013.01); *A61K 39/3955* (2013.01)

(58) Field of Classification Search
None
See application file for complete search history.

(56) References Cited

U.S. PATENT DOCUMENTS

| 4,342,747 A | 8/1982 | Liotet et al. |
| 9,248,151 B2 | 2/2016 | Bartorelli et al. |
| 2015/0010497 A1 | 1/2015 | Bartorelli et al. |

FOREIGN PATENT DOCUMENTS

| EP | 0743060 A1 | 11/1996 |
| JP | 2000159687 A | 6/2000 |
| WO | WO/95/00155 A1 | 1/1995 |
| WO | 9808603 A1 | 3/1998 |
| WO | WO/98/51316 A1 | 11/1998 |
| WO | WO/2006/029518 A1 | 3/2006 |
| WO | WO/2007/000648 A1 | 1/2007 |
| WO | WO/2007/128737 A1 | 11/2007 |
| WO | WO/2008/003688 A1 | 1/2008 |
| WO | WO/2009/046168 A1 | 4/2009 |
| WO | 2011064114 A1 | 6/2011 |
| WO | 2011087364 A1 | 7/2011 |

OTHER PUBLICATIONS

Brooks et al; "Potential prophylactic value of bovine colostrum in necrotizing enterocolitis in neonates: an in vitro study on bacterial attachment, antibody levels and cytokine production"; FEMS Immunology and Medic Microbiology, Elsevier Science B.V., Amsterdam, NL; vol. 48, No. 3, pp. 347-354 (Dec. 1, 2006).

Chandana et al.; "Humanized stem cell culture techniques: the animal serum controversy"; Humanized Stem Cell Culture Techniques: The Animal Serum Controversy; vol. 2011, No. 2011, pp. 1-14 (Jan. 1, 2011).

Chaumeil et al.; "Treatment of severe eye dryness and problematic eye lesions with enriched bovine colostrum lactoserum"; Advances in Experimental Medicine and Biology; vol. 350, pp. 599 (Jan. 1, 1994).

Hwang et al.; "Milk ingredients used for forming bone, promoting calcium absorption and for treating osteoporosis obtained by fractionating whey proteins generated during production of colostrum milk or chees"; WPI/Thomson; vol. 2006, No. 62 (Aug. 31, 2005).

(Continued)

*Primary Examiner* — Christine J Saoud
*Assistant Examiner* — Jegatheesan Seharaseyon
(74) *Attorney, Agent, or Firm* — Perkins Coie LLP; Viola T. Kung

(57) ABSTRACT

The present invention refers to a combination of growth factors, cytokines, antibacterial/antiviral factors, stem cell stimulating factors, complement proteins C3a/C4a, immunoglobulins and chemotactic factors. The invention also relates to a process for the preparation of said combination from serum, placenta or colostrum and to composition containing said combination for use in the treatment of conditions requiring tissue repair and regeneration and for the substitution of stem cell therapies.

8 Claims, 1 Drawing Sheet

(56) References Cited

OTHER PUBLICATIONS

International Search Report and Written Opinion of International Application No. PCT/EP2012/076962 with a mailing date of May 3, 2013.

Jeongrai et al.; "Effect of a growth protein-colostrum fraction on bone development in juvenile rats"; Bioscience Biotechnology Biochemistry, Japan Society for Bioscience, Biotechnology, and Agrochemistry, Tokyo, Japan; vol. 27, No. 1, pp. 1-6 (Jan. 1, 2008).

Jeongrai et al.; "Effect of colostrum basic protein from colostrum whey protein: increases in osteoblast proliferation and bone metabolism"; Journal of Food Science and Nutrition, Korean Society of Food and Nutrition, Pusan, KR; vol. 12, pp. 1-6 (Jan. 1, 2007).

Kaushal et al.; "Clinical evaluation of human placental extract (placentrex) in radiation-induced oral mucositis"; International Journal of Tissue Reactions; vol. 23, No. 3, pp. 105-110 (2001).

Kozlov; "Agent promoting and assisting wound healing—is obtd. by mixing cow's colostrum with water, sepg, and collecting fatty phase, whipping, melting, filtering, washing with hot water, and drying"; WPI/Thomson; vol. 1992, No. 30 (Oct. 15, 1991).

Landek-Salgado et al.; "Placental extract suppresses mouse models of autoimmunity"; http://jimmunol.orgjcgijcontentjmeeting abstract/184/1MeetingAbstracts/83.4 (Apr. 1, 2010).

Nitsch et al.; "The clinical use of bovine colostrum"; Journal of Orthomolecular Medicine; vol. 13, No. 2 (Jun. 1, 1998).

Pawan et al.; "Role of colostrum in gastrointestinal infections"; Indian Journal of Pediatrics, All India Institute of Medical Sciences, New Dehli, IN; vol. 75, No. 9, pp. 917-921 (Sep. 1, 2008).

Pouliot et al.; "Milk growth factors as health products: some technological aspects"; International Dairy Journal, Elsevier Applied Science, Barking, GB; vol. 16, No. 11, pp. 1415-1420 (Nov. 1, 2006).

Struff et al.; "Bovine colostrum as a biologic in clinical medicine: a review—Part II: clinical studies"; International Journal of Clinical Pharmacology and Therapeutics, Dustri-Verlag, Deisenhofen-Muenchen, DE; vol. 46, No. 5, pp. 211-225 (May 1, 2008).

Uruakpa et al.; "Colostrum and its benefits: a review"; Nutrition Research; vol. 22, No. 6, p. 762 (Jun. 1, 2002).

Won et al., "The effect of human placenta extract in a wound healing model"; Medline (Jul. 1, 2010).

Gao, "Skin, connective tissue and bone growth promoting composition"; WPI/Thomson; vol. 2005, No. 25, 1 page (Abstract)(Dec. 29, 2004).

Kim et al.; "Isolated whey protein fraction from colostrum of mammalia and food compostion comprising the fractuion are useful for treating and preventing osteoporosis"; WPI/Thomson; vol. 2006, No. 70, 1 page (Abstract)(Dec. 1, 2005).

Non-Final Office Action dated Oct. 22, 2015 for U.S. Appl. No. 14/369,146, pp. 1-17.

Bennett, G. et al., "A Peripheral Moneuropathy in Rat that Produces Disorders of Pain Sensation like those Seen in Man", (1988) Pain, vol. 33, pp. 87-107.

Caplan, A., et al., "Mesenchymal Stem Cells as Trophic Mediators", Journal of Cellular Biochemistry 98 (2006) pp. 1076-1084.

Garber, S., et al., "The Effect of Hyperglycemia on Pulpal Healing in Rats", JOE (2009), vol. 35, No. 1, pp. 60-64.

Zuk, P., et al., Multilineage Cells from Human Adipose Tissue: Implications for Cell-Based Therapies, Tissue Engineering (2001), vol. 7, No. 2, pp. 211-228.

COMBINATION OF GROWTH FACTORS, CYTOKINES, ANTIBACTERIAL/ANTIVIRAL FACTORS, STEM CELL STIMULATING FACTORS, COMPLEMENT PROTEINS C3A/C4A, IMMUNOGLOBULINS AND CHEMOTACTIC FACTORS

This application is a National Stage of International Application PCT/EP2012/076962, filed Dec. 27, 2012, published Jul. 4, 2013, under PCT Article 21(2) in English; which claims the priority of Italian Application Nos. MI2011A002432, MI2011A002433, MI2011A002435, MI2011A002439, MI2011A002440, MI2011A002441, MI2011A002443, MI2011A002445, and MI2011A002446, all filed Dec. 30, 2011. The contents of the above-identified applications are incorporated herein by reference in their entireties.

The present invention refers to a combination of growth factors, cytokines, antibacterial/antiviral factors, stem cell stimulating factors, complement proteins C3a/C4a, immunoglobulins and chemotactic factors. The invention also relates to a process for the preparation of said combination from serum, placenta or colostrum and to composition containing said combination for use in the treatment of conditions requiring tissue repair and regeneration and for the substitution of stem cell therapies.

BACKGROUND OF THE INVENTION

According to the current scientific literature, the therapeutic action of stem cells may be due to two mechanisms: differentiation of stem cells into resident cells and release of regenerative trophic factors by stem cells. The respective contributions of these two mechanisms remain to be clarified, although it has been suggested that stem cells do not develop into mature cells of the injured tissue, but they rather convey vital factors to this tissue, which can then return to proliferate and differentiate, regenerating itself (A I Caplan and J E Denni, Mesenchymal Stem Cells as Trophic Mediators. Bioch J. Cell 98:1076-1084, 2006).

Stem cell therapy has many problems related not only to the costs and technical and practical complications but also ethical and religious scruples.

Stem cell therapy is feasible only by injection or, in some cases, topically, and not orally The supernatant of cultured stem cells contains growth factors, cytokines, chemotactic factors etc., which are believed to be responsible for the beneficial effect of stem cell therapy on tissue growth and/or repair.

The use of the vital factors isolable from the supernatant of stem cells has, however, not only the same ethical problems of the use of the stem cells themselves but also very high costs.

It is known that some mammalian tissues and biological fluids, namely serum, placenta and colostrum, contain cytokines, growth factors, chemotactic factors, and other components usually found also in the supernatant of stem cell cultures.

Several therapeutic applications have been disclosed in the past for pure colostrum or of extracts or fractions thereof as well as for placenta extracts. For instance, a review of clinical uses of colostrum is reported in Alternative Medicine Review 8(4), 2003, page 378 and in Int. J. Clin. Pharmacol and Therap., 46(5), 2008, 211-225 and in International Dairy Journal, 16, 2006, 1415-1420.

Therapeutic uses of colostrum or fractions thereof are also reported in EP 743060, WO 98/51316, WO 94/16675, WO 98/36759, WO 95/00155, WO 2007/000648, FR 2487676, WO 98/14473, WO 99/64022, WO 2008/103023 and in WO 2006/029494. The latter discloses the extraction of growth and differentiating factors from colostrum but the process disclosed necessarily involves the loss of important components (e.g. cytokines, stem cell stimulating factors, chemiotactic factors and antibacterial/antiviral factors) of pure colostrum. None of the prior art documents discloses compositions derived from easily available mammalian sources containing most of if not all components of stem cell cultures supernatant, as a substitute for stem cell therapy.

DESCRIPTION OF THE INVENTION

Figure 1A:
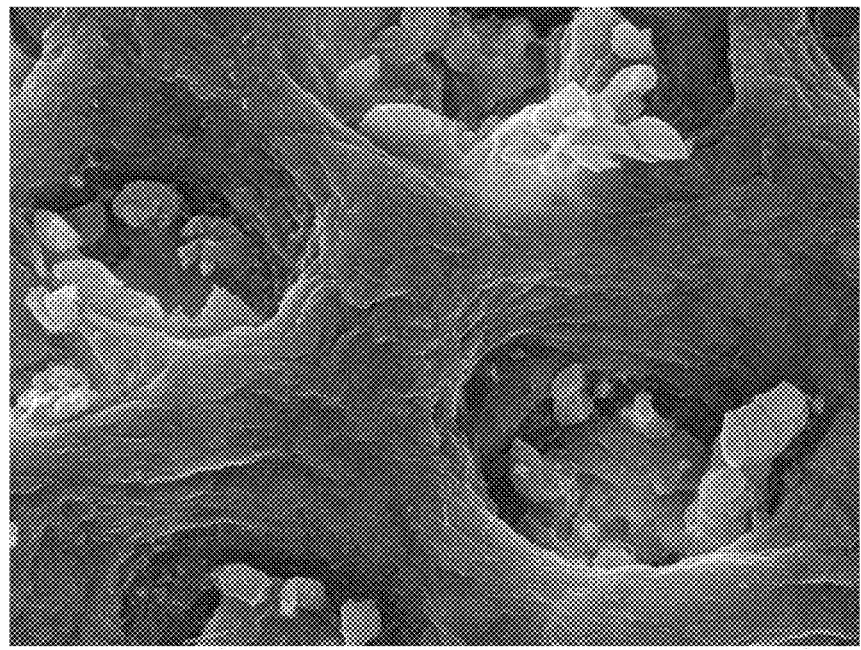
FIG. 1A shows scanning electronic microscope image of control animals.

It has been found that a combination of growth factors, cytokines, antibacterial/antiviral factors, stem cell stimulating factors, complement proteins C3a/C4a, immunoglobulins and chemotactic factors is particularly effective in the treatment of a number of pathologies thanks to their multifunctional activities on different biological targets.

The combination of the invention is characterized by a content of:

Cytokines: from about 50 to about 300 pg/mg, preferably from 47.81 to 264.56;

Growth factors: from about 650 to about 1900 pg/mg, preferably from 670.80 to 1869.40;

Chemotactic factors: from about 2 to 20 pg/mg;

Stem cell stimulating factors: from about 100 to 1200 pg/mg, preferably from 136 to 1120;

Antibacterial/antiviral factors: from about 30 to 80 µg/mg, preferably from 21.30 to 71.50;

Complement C3a/C4a proteins: from about 1 to 5 pg/mg, preferably from 1.10 to 2.70;

Immunoglobulins: from about 0.3 to 0.9 mg/mg, preferably from 0.35 to 0.85.

The cytokines present in the combination of the invention, hereinafter referred to as PMF Ab, are reported in Table 1:

TABLE 1

Cytokines in PMF Ab (pg/mg)

|  | Val min | Val max |
|---|---|---|
| IL-1° | 0.80 | 2.90 |
| IL-1b | 0.02 | 0.09 |
| IL-2 | 0.75 | 5.00 |
| IL-4 | 0.04 | 0.17 |
| IL-6 | 0.10 | 1.20 |
| IL-8 | 0.50 | 2.50 |
| IL-9 | 0.50 | 3.60 |
| IL-10 | 0.50 | 2.80 |
| IL-12 | 0.50 | 2.00 |
| IL-15 | 1.10 | 4.30 |
| IL-17 | 15.00 | 150.00 |
| INF gamma | 3.00 | 30.00 |
| TNFα | 15.00 | 30.00 |
| IL-1 Ra | 10.00 | 30.00 |
| Total | 47.81 | 264.56 |

The growth factors present in the combination of the invention are reported in Table 2:

TABLE 2

| Growth factors in PMF Ab (pg/mg) | | |
|---|---|---|
| | Val min | Val max |
| TGF-β1 | 150.00 | 300.00 |
| IGF-1 | 300.00 | 800.00 |
| NGF | 1.00 | 10.00 |
| PDGF | 5.00 | 100.00 |
| EGF | 4.80 | 9.40 |
| BMP2 | 15.00 | 50.00 |
| b.FGF | 100.00 | 200.00 |
| FGF-2 | 5.00 | 20.00 |
| HGF | 40.00 | 80.00 |
| VEGF | 50.00 | 300.00 |
| Total | 670.80 | 1869.40 |

The stem cell stimulating factors present in the combination of the invention are reported in Table 3:

TABLE 3

| Stem cell stimulating factors in PMF Ab (pg/mg) | | |
|---|---|---|
| | Val min | Val max |
| G-CSF | 10.00 | 20.00 |
| GM-CSF | 100.00 | 1000.00 |
| LIF | 15.00 | 50.00 |
| SCF | 1.00 | 10.00 |
| SDF-1 | 10.00 | 40.00 |
| Total | 136.00 | 1.120.00 |

The chemotactic factors present in the combination of the invention are reported in Table 4:

TABLE 4

| Chemotactic factors in PMF Ab (pg/mg) | | |
|---|---|---|
| | Val min | Val max |
| EOTAXIN | 1.00 | 15.00 |
| MCP-1 | 1.00 | 5.00 |
| total | 2.00 | 20.00 |

The antibacterial/antiviral factors present in the combination of the invention are reported in Table 5

TABLE 5

| Antibacterials/Antivirals in PMF Ab (microgram/mg) | | |
|---|---|---|
| Transferrin | 0.50 | 1.00 |
| Lactoferrin | 0.80 | 2.50 |
| Lysozyme | 10.00 | 40.00 |
| Lactoperoxydase | 10.00 | 30.00 |
| total | 21.30 | 73.5 |

The complement C3a C4a proteins present in the combination of the invention are reported in Table 6.

TABLE 6

| Complement proteins in PMF Ab | | |
|---|---|---|
| | Val min | Val max |
| C3A | 0.20 | 0.70 |
| C4A | 0.90 | 2.00 |
| Total | 1.10 | 2.70 |

The immunoglobulins present in the combination of the invention are reported in Table 7.

TABLE 7

| Immunoglobulins in PMF Ab (mg/mg) | | |
|---|---|---|
| | Val min | Val max |
| IgG | 0.20 | 0.50 |
| IgA | 0.10 | 0.20 |
| IgM | 0.05 | 0.15 |
| Total | 0.35 | 0.85 |

The data reported in Tables 1-7 were obtained by commercially available sandwich ELISA methods specific for bovine molecules and flexible Bio-Plex® system (Bio-Rad Lab., Hercules, Calif., USA). The term "about" means a variation of ±10%, preferably ±5% of the given value.

The main physiological roles of the components of the combination are reported below.

Complement Proteins C3/C4:

The complement consists of circulating proteins able to interact with the biological membranes and with specific receptors situated on the surface of various cell types, which induce inflammatory reactions that help combat infection.

Growth Factors

TGF-β1—TRANSFORMING GROWTH FACTOR: stimulates the production of Class A immunoglobulins, which are responsible for immune defences in the mucosa. Modulates cell proliferation and stimulates the deposit of extracellular matrix.

EGF—EPIDERMAL GROWTH FACTOR: regulates the development of the mucosa. Promotes the formation of epithelial cells.

IGF 1—INSULIN-LIKE GROWTH FACTOR: modulates cell proliferation, adhesion and migration and induces maturity of the mucosa.

VEGF—VASCULAR ENDOTHELIAL GROWTH FACTOR: stimulates blood vessel production. Presents mitogenic activity and activation of vascular permeability.

FGF-b—FIBROBLAST GROWTH FACTOR BASIC: stimulates proliferation of cells of mesenchymal origin such as fibroblasts, endothelial cells, astrocytes and keratinocytes. It also acts as a chemotactic factor.

GH—GROWTH HORMONE: general growth factor of all tissues.

GHRF—GROWTH HORMONE RELEASING FACTOR: stimulates the release of GH. required for normal postnatal growth, bone growth, regulatory effects on protein, carbohydrate, and lipid metabolism.

NGF—NERVE GROWTH FACTOR: stimulates activity and regulates growth and differentiation of the sympathetic system.

PDGF-PLATELET DERIVED GROWTH FACTOR: growth/differentiation of cells of mesodermal origin BMP-2—BONE MORPHOGENETIC PROTEIN 2: Development of bone and cartilage, cardiac cell differentiation.

Chemotactic Factors

EOTAXIN: binds to the chemokine receptors to recruit eosinophils to inflamed tissues.

MCP-1 Monocyte chemotactic factor-1: promotes aggregation of monocytes to inflamed tissues.

Cytokines

IL-1Ra inhibits the activities of interleukin 1 alpha and interleukin 1-beta, modulating a variety of IL 1 related immune and inflammatory responses.

IL-2 induces proliferation of T lymphocytes.

IL-4 possesses anti-inflammatory activity.

IL-6 stimulates innate and adaptive immunity.

IL-9 is a regulator of haemopoietic cells, stimulates cell proliferation and prevents apoptosis.

IL-17 regulates the activities of NF-KB and boosts nitric oxide (NO) production.

IL-10 has pleiotropic effects in immunoregulation and inflammation. Improves B cell survival, and therefore antibody production. Studies conducted on knock-out mice demonstrate that this protein is essential in immunoregulation of the mucosa. IL-12 stimulates T and natural killer cells.

IL-15 regulates T and natural killer cell activation and proliferation.

Interferon-gamma has known antiviral, antitumoral and immunoregulatory activities. It is a powerful macrophage activator and activates cell-mediated activity against bacteria and viruses.

TNF-α—Tumour necrosis factor stimulates the migration of neutrophils and monocytes to the site of infection.

Stem Cell Stimulating Factors

GM-CSF—granulocyte colony stimulating factor: is involved in the stimulation and peripheral dismission of immune progenitors from the bone marrow.

LIF—Leukemia inhibitory factor: pleiotropic cytokine with roles in several different systems, involved for instance in the induction of hematopoietic differentiation in normal and myeloid leukemia cells, induction of neuronal cell differentiation, regulator of mesenchymal to epithelial conversion during kidney development.

SCF—Stem cell factor: acts in utero in germ cell and neural cell development and hematopoiesis.

SDF-1—stromal derived factor-1: acts as a chemotactic factor of stem-progenitor cells expressing the CXCR4 ligand.

Antibacterials

Transferrin: delivers iron to red blood cells and prevents bacteria and viruses binding to iron.

Lactoferrin: deprives bacteria and viruses of iron required for their growth.

Lysozyme: has antibacterial effects in view of its enzymatic activity and as a consequence of its cationic and hydrophobic properties.

Lactoperoxydase: inhibits bacterial metabolism by oxidation of essential protein SH groups.

The combination of the invention may be prepared by extraction of colostrum, serum from pre-partum mammals or placenta according to the methods detailed below.

The serum has the highest peak of the factors in the last days before the birth, colostrum in the first hours after birth and no later than the 6th hour.

After 12 hours of delivery, the factors in colostrum decrease significantly and at 24 h many of them are no longer detectable.

These factors are genetically highly conserved in different species and therefore it is possible to use factors isolated from other mammalian species such as cattle, horses, camels, marine mammals, etc.

The factors are controlled with ELISA assays, specific for the species, even if the interspecies cross-reaction is very high because the factors are phylogenetically very conserved and are therefore qualitatively measurable also with ELISA used for different species (eg human-bovine and vice versa).

It is not necessary to add antibacterial preservatives to colostrum, serum or placenta since the extraction procedure allows the preparation of a product having a very low bacterial count (<40 c.f.u), much lower than the value admitted for the considered uses (<1000 c.f.u.). The presence of pyrogens for oral or topical administration is irrelevant.

Extraction from Mammalian Serum

The serum of mammals pregnant females has the highest peak of the components of the combination of the invention in the last days before the delivery or parturition, usually in the last 5-15 days.

A typical procedure for the preparation of the combination of the invention is described.

1 liter of blood is drawn in 4 days for a total of 4 samples to prevent damage to the animal, preferably bovine or equine.

Serum is separated from the blood at room temperature for 24 h and then centrifuged to squeeze the clot.

Serum is recovered (approximately 30/40% of the total volume) and is then subjected to the following steps.

Ultrafiltration 300,000 Da:

The serum sample (frozen at −20° C.) obtained by coagulation and centrifugation from mammalian blood is thawed at room temperature and diluted with 2 volumes of demineralized water. The resulting solution is ultrafiltered through a Millipore BIOMAX® PELLICON® (ultrafiltration cassette with polyethersulfone and untracel regenerated cellulose membrane) 300,000 Da plane tangential flow membrane in polyethersulfone at Pi of 0.5 to 1 bar, in a cold room at 4° C.

The retentate and a fraction corresponding to about 1:10 of the permeate are transferred into a 1000 Da dialysis tube from Spectrum SPECTRAPOR® (dialysis membrane) in regenerated cellulose and dialyzed against demineralized water.

Ultrafiltration 5,000 Da:

The remaining permeate is ultrafiltered through a 5000 Da membrane. The permeate from the 300,000 Da ultrafiltration is concentrated on a 5000 Da plane tangential flow membrane Millipore BIOMAX® PELLICON® in polyethersulfone at Pi from 0.5 to 1 bar, cold room at 4° C.

The retentate is transferred to a 1,000 Da dialysis tube in regenerated cellulose from Spectrum SPECTRAPOR® and dialyzed against demineralized water (this dialysis also removes the preservatives). The product is then immediately lyophilized.

Extraction from Placenta

Bovine, equine or suine placenta is preferably used.

Homogenization:

The placenta (frozen at −20° C.) is thawed at room temperature, cut into small pieces, washed with copious amounts of cold (4° C.) physiological saline (NaCl 0.9%) and homogenized using a Siramm cutter in a lysis buffer having the following composition: Tris/HCl 50 mM, EDTA 25 mM, TRITON® X-100 (octylphenol ethylene oxide condensate) 0.001% at pH 7.4. NaCl to a concentration of 0.9% is added to the suspension obtained. The suspension is stirred (magnetic stirrer) for 2 hours and maintained static overnight in a cold room at 4° C.

Centrifugation

The suspension was centrifuged at 13,000 rpm with a Sorvall RC6 and rotor SLA 15000 for 45 minutes at 4° C. The supernatant from the centrifugation is recovered, vacuum pre-filtered on DICALITE® (natural diatomite earth) and regenerated cellulose filters from 0.45 µm to 0.22 µm.

Ultrafiltration 300,000 Da

The product is filtered and ultrafiltered through a 300.000 Da Millipore BIOMAX® PELLICON® plane tangential flow membrane in polyethersulfone at Pi of 0.5 to 1 bar, in a cold room at 4° C.

Ultrafiltration 5,000 Da

The permeate from the 300,000 Da ultrafiltration is concentrated on a 5000 Da Millipore BIOMAX® PELLICON® flat tangential flow membrane in polyethersulfone at Pi of 0.5 to 1 bar, in a cold room at 4° C. The retentate is transferred to a 1,000 Da dialysis tube from Spectrum SPECTRAPOR® in regenerated cellulose and dialyzed against demineralized water and then immediately lyophilized.

Extraction from Colostrum

Bovine colostrum is preferred, in particular from Holstein (Friesian) and Guernsey cows. It has been demonstrated that these cows produce the colostrum with the highest concentration of growth factors, immune modulators, chemotactic factors and antibacterial/antiviral factors. The cows are preferably calving for the second or third time. Colostrum is preferably collected not later than the $5^{th}$-6th hour after calving, preferably colostrum collected one hour after calving, because the highest concentration of active substances is found during that period, while from the sixth hour onwards the active factors decline rapidly (only 20% are present 24 hours after calving).

The colostrum collected is tested for tuberculosis, cytotoxicity on cell cultures, mycoplasma, prions and human and bovine viruses.

The colostrum in the udder cistern is practically sterile, but once milked, despite all precautions, due to the high concentration of growth factors, its bacteria count rises very rapidly during freezing and thawing, which are rather slow processes in view of the high density of colostrum in the first few hours.

The colostrum is then diluted with saline solution: this dilution not only gives better filtration without clogging the filter pores, but above all allows the release of active factors bonded to fats and casein. The colostrum thus diluted undergoes tangential microfiltration (ceramic membranes with a cut-off between 2 and 6 µm, temperature 5/20° C., transmembrane pressure between 0.2 and 2 bars), which may be repeated, to obtain an opalescent solution free of casein, fat matrix and milk proteins. All these substances constitute over 90% of the allergic content of colostrum and cow's milk. The solution is then passed through membranes, or alternatively a molecular sieve with a cut-off at 300,000 daltons, for further purification of the active factors, all weighing less than 200,000 daltons.

The solution is then dialysed by ultrafiltration (cut-off 1000/2000 daltons) at high pressure, and then immediately freeze-dried. The result is a preservative-free, anallergic powder (casein and lactoalbumin are responsible for over 95% of allergies to cow's milk) of very high solubility, with the maximum possible concentration of active factors and characterised by a very low bacterial count (<40 CFU).

The products obtained from serum, placenta or colostrum may be used separately or they may be pooled together. The products will in any case meet the quantitative ranges specified in Tables 1-7.

The combination of the invention is advantageously used, either orally or topically, in the treatment of conditions requiring tissue repair and regeneration, for the substitution of stem cell therapies. In particular, the combination of the invention, containing the same components of the supernatant of stem cell cultures, are useful for the oral treatment of:

autoimmune diseases, specifically of diabetes of type I, multiple sclerosis, arthritis, autoimmune hepatitis, ulcerative colitis;

neuropathic pain;

gastro-intestinal diseases such as necrotising acute enterocolitis, Chron's diseases, gastro-esophageous reflux, enterocholitis induced by AIDS, irritable bowel syndrome, infective colitis, spastic colitis, colitis induced by antibiotics, hiatal hernias, short esophagus syndrome and the like;

osteoporosis;

The combination of the invention is also useful for the topical treatment of:

different forms of alopecia;

corneal lesions;

wounds, burns, skin ulcers;

lesions of the oral mucosa.

For the oral treatment, the combination of the invention will be formulated with suitable carriers and excipients in suitable dosage forms such as capsules, tablets, powders, granulates, suspensions, functional food and similar forms conventionally used in the nutraceutical field.

The daily dosage of the combination will depend on the kind and severity of the condition to be treated as well as on the patient's conditions, age and sex. It will generally range from 10 to 30 g daily, in one or more administrations, typically three to four administrations.

For the topical treatment, suitable administration forms include creams, ointments, gels, powders, lotions, mouthwashes, patches, comprising typically from 10 to 20% by weight of the combination of the invention. The combination of the invention obtained from colostrum, serum or placenta, if desired may be coated for specific applications, for instance in controlled releases forms, preferably into microspheres.

The formulations may contain other ingredients useful for specific uses. For example, for the treatment of wounds and ulcers, zinc oxide and *Arnica montana* extract may be suitable added.

The invention will be described in more detail in the following experimental part, given by way of examples.

EXAMPLE 1

Autoimmune Disease

The effects of the preventive oral administration of PMF Ab were evaluated on different models of autoimmune diseases such as Experimental Allergic Encephalomyelitis (EAE), type I diabetes, ulcerous cholitis induced by TNBS, hepatitis induced by ConA and arthritis induced by adjuvant and by collagen.

EXAMPLE 1a

Experimental Allergic Encephalomyelitis (EAE)

EAE was induced in female SJL mice 6-7 weeks old as disclosed in J. St. Louis et al. Mice were immunised with 75

µg of proteolipidic protein PLP (139-151) (Genemed synthesis, San Francisco Calif.), emulsioned in CFA containing 0.6 mg/ml of *Mycobacterium tuberculosis* H37RA (Difco, Detroit, Mich., USA) to give a 1:1 emulsion. Each mouse received 200 µl of the emulsion sc in four sites proximal to axillar and inguinal lymphonodes. The pertussis toxin (Calbiochem, Nottingham, UK) used as co-adjuvant, dissolved in water at the concentration of 2 µg/ml was administered ip in a volume of 100 µl at day 0 and day 2 after immunisation. The clinical evaluation was carried out according to the following score: 0=no sign of disease, 1=flaccid tail, 2=moderate paraparesis, 3=severe paraparesis, 4=moribund, 5=death.

Two groups of 6-10 mice each were administered orally respectively PMF Ab at the dose of 0.1 g/mouse and its vehicle (water) starting from day 0.

PMF Ab was dissolved in water at a concentration of 0.1 mg/ml and administered at a final volume of 0.25 ml.

Results

Effects of P.M.F. Ab on the Development of EAE Induced by PLP (Proteolipid Protein) and Pertussis Toxin.

After 42 days of treatment with P.M.F. Ab (25 micrograms), the disease developed in only 2 out of 6 mice (33.3%) compared to 9 out of 10 mice in the group of mice treated with vehicle (90%). In addition, mice treated with P.M.F Ab developed a milder course of illness with a lower average cumulative score and a shorter duration of the disease than the mice treated with the vehicle (Table 8).

TABLE 8

Effects of PMF Ab on the clinical parameters in EAE induced in SJL mice by PLP

|  | cumulative score | duration | Incidence |
|---|---|---|---|
| Average |  |  |  |
| P.M.F. Ab | 9.2 | 4.3 | 33.3 |
| Vehicle | 29.4 | 13.6 | 90.0 |
| Dev. st |  |  |  |
| P.M.F. Ab | 15.4 | 7.2 |  |
| Vehicle | 18.6 | 8.5 |  |
| T-test |  |  |  |
| P.M.F. Ab | 0.042 | 0.040 |  |

EXAMPLE 1b

Type I Diabetes

Diabetes mellitus type 1 (DM type 1) is a multi factorial syndrome caused by the failure of endogenous insulin production as a result of immune response of auto reactive T-lymphocytes and macrophages against pancreatic beta cells of Langerhans.

40 mg/kg of streptozotocin (STZ) were administered ip for 5 consecutive days to male C57B16J mice 7-8 weeks old.

Two groups of 7-8 mice were treated orally from day 0 to day 21 six times a week with PMF Ab at a dose of 0.2 g/mouse or with the vehicle. PMF Ab was dissolved in water at a concentration of 0.4 mg/ml and administered at a final volume of 0.5 ml.

Mice were checked once a week measuring glycemia. Diabetes was diagnosed when glycemia exceeded 11.8 mmol/L.

Results

As expected, the mice belonging to the control group treated with vehicle developed hyperglycemia 2 weeks after the last STZ injection and reached 100% incidence within 3 weeks.

In contrast, prophylactic treatment with P.M.F. Ab has completely protected mice from STZ-induced hyperglycemia.

Treatment with P.M.F.Ab for 21 days at a dose of 0.2 g/mouse was well tolerated.

EXAMPLE 1c

Ulcerative Colitis Induced by TNBS

To study the possible effects of P.M.F.Ab on this organ-specific autoimmune pathology the experimental model of IBD induced by TNBS was used.

In the model, a single administration of TNBS is responsible for the appearance, within 4 days, of a disease with clinical immunohistological features very similar to those found in human inflammatory bowel disease such as Crohn's disease and ulcerative colitis.

Colits was induced in 20 male Balb/C mice, weighing 20-25 g, by a single intra-cholic administration at day 0 of a solution of 4 mg of trinitrobenzene sulfate (TNBS) in 0.1 mL of 50% ethanol.

10 animals were treated per os with PMF Ab at the dose of 0.2 g/mouse and 10 animals (controls) were treated with the corresponding vehicle (water), daily for 4 consecutive days starting from induction (days 0, 1, 2 and 3).

Animals were sacrificed at day 4 and the mucosal damage (ADM) was evaluated on a 7 cm distal colon segment. The evaluation of the score of macroscopic damage (SDM) was evaluated according to the following criteria: 0=no damage; 1=localised hyperemia and/or oedema; 2=linear ulcer< than half the colon width; 3=linear ulcer> than half the colon width; 4=circular ulcer<1 cm; 5=circular ulcer from 1 to 2 cm; 6=circular ulcer>2 cm.

Results

As expected, in the control group there was a significant reduction in body weight between day 0 and day of sacrifice (−18%), an increase of the weight of the colon (0.47±0.16 g), and a marked damage in colon mucosa (average ADM=68±57 mm$^2$, Table 9).

Treatment with PMF Ab at a dose of 0.1 g/mouse showed a significant reduction in the area of necrosis and a positive trend towards the decrease of the colon weight.

TABLE 9

Effects of PMF Ab on clinical parameters in TNBS-induced colitis in mice.

|  | Stool score | Colon weight | Necrosis area |
|---|---|---|---|
| P.M.F. Ab | 0.9 | 0.342 | 19.98 |
| Vehicle | 1.8 | 0.469 | 67.61 |
| Sham | 0 | 0.130 | 0 |
| P.M.F. Ab | 1.05 | 0.08 | 12.71 |
| Vehicle | 1.67 | 0.16 | 57.09 |
| Sham |  | 0.05 |  |
| P.M.F. Ab | 0.217 | 0.053 | 0.027 |

EXAMPLE 1d

Autoimmune Hepatitis

The experimental model of ConA-induced hepatitis in NMRI mice was used.

In this model, the single injection of Con A is sufficient to develop immune-mediated liver injury, evaluated by glutamate-pyruvate transaminase (GPT) levels in plasma.

20 male albino NMRI mice, 6-7 weeks old, were inoculated iv with 20 mg/kg of Con A (Sigma Chemical, St. Louis, Mo.) in sterile PBS.

10 animals were treated per os with PMF Ab at the dose of 0.2 g/mouse and 10 animals (controls) were treated with the corresponding vehicle (water), 24 hours before and 1 hour before Con A inoculation.

The animals were sacrificed 8 h after Con A injections and glutamate-pyruvate transaminase was determined in plasma.

Results

After the sacrifice, signs of acute liver damage were found in all mice of the control group injected with Con A and treated with water. These animals had, in fact, marked increases in plasma GPT, reaching an average of 1556±869 U/I (Table 10). The treatment with PMF Ab at a dose of 0.2 g/mouse significantly reduced the GPT levels in the plasma (p.01 by Student t-test).

TABLE 10

GPT values in Con A-treated mice

| GPT | Vehicle | P.M.F. Ab |
|---|---|---|
| MEDIA | 1555.9 | 442.8 |
| DEV. ST. | 868.7 | 622.4 |
| T-test | | 0.004 |

EXAMPLE 1e

Arthritis Induced by Collagen Type II in Mice DB/1j (CIA)

The disease can be induced in mice and in rats by intradermal injection of type II collagen homologous or heterologous emulsified in complete Freund's adjuvant.

The effects of PMF Ab were evaluated by testing the PMF Ab at a dose of 0.2 g/mouse. The animals were observed every other day for the evaluation of significant clinical parameters.

40 male DBA/j1 mice, 8-9 weeks old, were used. The disease was induced by means of an intra-dermal inoculation of an emulsion of 100 μg of bovine collagen type II in 100 μl emulsified in Freund's complete adjuvant (CFA) (Sigma, Milano, Italia). The animals received a second booster at day 21 post-immunization by means of an intradermal inoculation of 100 μg of Collagen type II in a total volume of 100 μl of Freund's incomplete adjuvant.

Four groups of 10 animal each were respectively treated per os daily with PMF Ab (0.2 g/mouse), with the corresponding vehicle (sterile PBS) and with Dexametasone (0.3 mg/kg), starting from induction day until day 30 post-induction. A further group of 10 healthy mice was added (Sham). The clinical index of arthritis was evaluated by scoring each animal's paw (thickness, swelling/oedema, involvement of one, two or more joints)

Results

Animals of the control group developed arthritis-associated clinical signs within 29 days after induction, showing a gradual increase both in the clinical score of disease and in paw thickness, reaching a maximum value at day 40. No difference was found between the increase in body weight in the treated group and in the control group.

PMF Ab at a dose of 0.2 g/mouse significantly reduced the clinical score of disease (p<0.05 vs. vehicle by t-test) from day 30 to day 33 post-induction, with a positive trend from day 34 until the end of the study.

Similar results were obtained in Lewis rats, in a model of adjuvant-induced arthritis.

EXAMPLE 2

Neuropatic Pain

EXAMPLE 2a

Animal Experiments

The model of chronic constriction injury (CCI, Bennett and Xie, 1988) was used because it produces a robust Wallerian degeneration and inflammation. In addition, since some fibers survive the injury, there remains the possibility to conduct behavioral tests to assess the pain symptoms.

The neuropathy was induced in C57BL/6J male mice of nine weeks, weighing 20-25 g. Under barbiturate anesthesia, with the aid of a dissecting microscope, the sciatic nerve was exposed at the middle of the right paw and before the trifurcation and three loose ligatures were made around it, taking care to preserve the epineural circulation.

False-operated animals (exposure of the nerve without ligation) served as a control.

The thermal hyperalgesia was evaluated according to the procedure of Hargreaves modified for the rat, using a tool Plantar test. In short, the mice are placed in small cages of Plexiglas and a radiant heat source of constant intensity is directed towards the central part of the hind paw. The time (seconds) from the activation of source to the withdrawal of the paw was recorded.

PMF Ab was administered orally at a dose of 0.4 g/mouse every day from the time of injury for three weeks.

Results

The results are reported in the following Table 11

| DAYS | | 14 | 21 | 28 |
|---|---|---|---|---|
| LATENCY THRESHOLDS (DAYS) | Controls | 18 | 20 | 18 |
| | Neuropathy | 12 | 14 | 18 |
| | Treatment with PMF Ab | 8 | 7 | 9 |

Treatment with PMF Ab led to an increase in the thresholds of analgesia that were significantly higher than that of neuropathic animals treated with diluent already from day 21 to reach the same levels of normal animals at day 28 of treatment.

EXAMPLE 2b

Clinical Experiments in Humans

Six subjects 4 males and 2 females, suffering from post-herpetic pain after herpes from two to three years, were treated every day for thirty days with PMF Ab orally (10 g/daily).

Pain was assessed subjectively using the VAS (Visual Analogue Scale) and objectively, using a test of hyperalgesia represented by stimulation with von Frey filaments of the areas affected by the disease and its surrounding areas.

The study was "open", assessing the levels of pain and hyperalgesia from baseline (start of treatment).

Subjects treated with PMF Ab experienced an improvement of the subjective pain sensation, with a variation in VAS after 15 days of treatment from 6.0 to 2.0. The latter value was maintained until the end of treatment (30 days). Stimulation with von Frey filament (sequence of pressures from 0.05 to 140 g) resulted in significantly different curves of VAS/applied force, indicating a progressive improvement of hyperalgesia from the twentieth day of treatment until the end.

EXAMPLE 3

Treatment of Anorexia

Twenty female patients aged between sixteen and thirty years, suffering from anorexia nervosa with weight loss between 15 and 30% of what is considered normal for the age and the physical structure, were treated daily with 40 g of PMF Abby the oral route. It is interesting to note that all patients, despite the serious nutritional problems, agreed to take the product since they were reassured that the product itself does not increase body fat but only the muscular mass, positively influencing cardiovascular, respiratory and neurological parameters.

After three months of adjuvant therapy, 50% had recovered more than 30% of body weight with a significant improvement in physical and mental abilities. The blood chemistry parameters were normalized.

Surprisingly, 25% of these patients even resumed to eat normally with restitutio ad integrum of body mass. The remaining 25% did not respond.

EXAMPLE 4

Osteoporosis

The effect of P.M.F. Ab was evaluated in vitro and in vivo assays for proliferation and differentiation of osteogenic mesenchymal stem cells, progenitors of bone, and osteoblasts.

EXAMPLE 4a

In Vitro Tests

Proliferation

The effects of P.M.F. Ab on cell proliferation were evaluated using human osteoblast (Saos-2 and MG-63) cells and human mesenchymal stem cells, as a model osteoblast precursor (human Adipose tissue-derived Stem Cells, hASC).

The ASC were isolated (Zuk P A et al., 2001) from 6 donor volunteers and kept in control medium (DMEM supplemented with sodium pyruvate, 10% FCS, 100 U/ml penicillin, 100 mg/ml streptomycin and 250 ng/ml amphotericin B). Osteoblasts line Saos-2 (ATCC number: HTB-85) and MG-63 (ATCC number: CRL-1427) were purchased from ATCC. Saos-2 and MG-63 were maintained respectively in McCoy'5A (Gibco, Life Technologies) with 15% FBS, and in DMEM with 10% FCS.

The cells were seeded in 96-well plates and subjected to MTT test on days 1, 3, 5 and 7 and were maintained in a humidified atmosphere of 5% CO2 in air at 37° C. PMF Ab shows a potent dose-dependent proliferative effect on all the lines studied, ceiling at a concentration of 5 mg/ml.

EXAMPLE 4b

In Vivo Tests in Ovariectomized Female Rats

The effects of PMF Ab on bone mass was investigated in an animal model of osteopenia (surgical Oophorectomy) in mature rat comparable with human postmenopausal osteoporosis.

Sprague-Dawley rats 5 months old subjected to surgical bilateral oophorectomy were used. The effects of PMF Ab on bone mass were assessed by measuring both planar and volumetric femoral bone mineral density (BMD) (distal metaphysis and medial diaphysis) by means of computerized bone mineral density (DXA) and bone computed tomography (pQCT). mRNAs for interleukin-8, the RANKL factor and osteprotegine peptide were assessed as biochemical markers of bone turnover. The rats were treated for 60 days from the time of ovariectomy with PMF Ab orally (2-4-8 g/kg) for 5 days/week. Both BMD and biochemical parameters of bone turnover were assessed both before (T0), during (T30) and at the end of treatment (T60).

The treatment induced a dose dependent-recovery from osteopenia and a normalization of the related biochemical parameters.

EXAMPLE 5

Treatment of Acute Necrotising Colitis (NEC)

A model of NEC in pigs, identical to macroscopic and microscopic pathological effects in the human, was used.

Figure 1B:
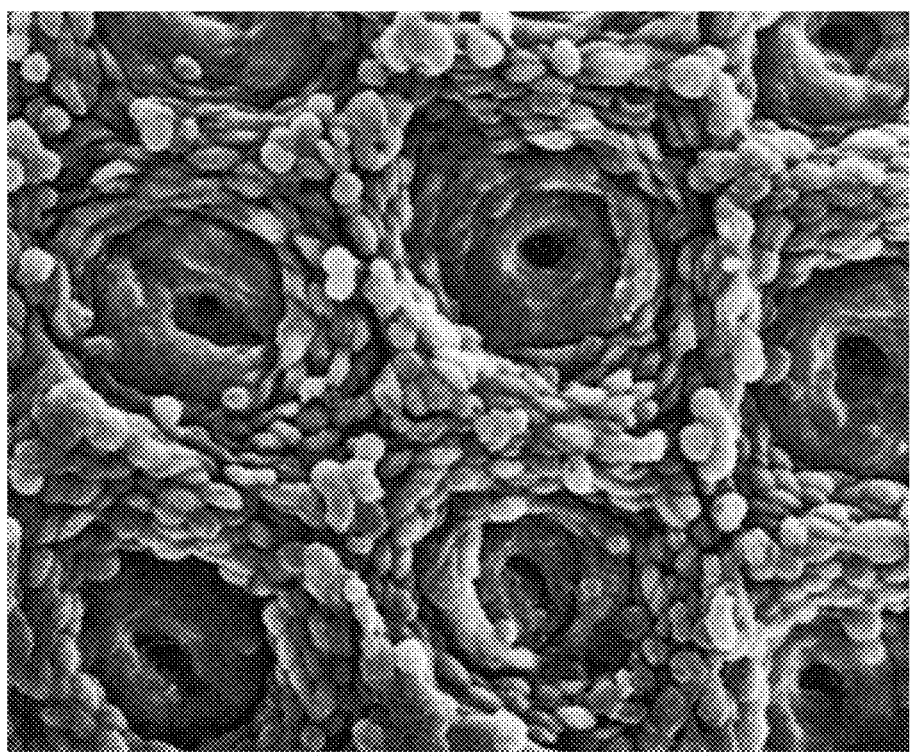
FIG. 1B shows scanning electronic microscope image of animals after treatment with PMF Ab.

1. Comparison of Subjects Fed with Milk Formula+PMF Ab and Subjects Only Fed with Milk Formula The subjects fed with formula milk plus 20 g/die of PMF Ab have a regular growth comparable to that of the control group maintained under sow. The piglets fed from birth with only milk formula, after the first day of regular growth, exhibit from the second day prostration, locomotor ataxia, interruption of spontaneous alimentation, regurgitation and diarrhea. After a quick weight loss within a further 24-48 hours, the animals died. Histopathological examination of the various sections of the large intestine taken post mortem allowed the diagnosis of lethal acute necrotizing enterocolitis, confirmed by electron microscopy (FIGS. 1a and 1b).

2. Comparison of Groups Fed with Increasing Doses of PMF Ab

Subjects fed with formula milk+20 g/day of PMF Ab: regular growth, entirely comparable to that of the control group maintained under sow.

Subjects fed with milk formula+1 g/day of PMF Ab: the subjects slim quickly and within a further 24-48 hours, the entire group die.

Group of subjects fed with milk formula+5 g/day of PMF Ab: a condition of real cachexia occurs and within a few days the death of the entire group. The histopathological examination of several sections of the large intestine taken from groups of subjects fed respectively with 1 g/day and 5 g/day of PMF Ab, allows the diagnosis, also in this case, of a lethal acute necrotizing enterocolitis.

Group of subjects fed with milk formula+10 g/day of PMF Ab: diarrhea occurs in all the subjects. On the 13th-14th day, the pathological manifestations worsen suddenly and the animals die within a few hours of acute necrotizing colitis.

Group of subjects fed with milk formula+15 g/day of PMF Ab: regular growth, with no observed pathological manifestation of any kind, but the performance of growth are slightly lower than those from the group of subjects fed with milk formula+20 g/day of PMF Ab.

Group of subjects fed with formula milk+20 g/day of PMF Ab (maintained until day 15): regular growth, entirely comparable to that of the control group maintained under sow.

3. Comparison of Subjects Fed with Milk Formula+PMF Ab and Subjects Fed with Only PMF Ab+Sugar Solution Ad Libitum Piglets fed ad libitum with a sugar solution+20 g/day of PMF Ab, without the addition of milk formula, do not have any kind of disease but lose weight steadily, a sign of an insufficient supply of nutrients provided by the sugar solution in place of the milk formula. These individuals eventually die, but the colon, at the histopathological examination, is surprisingly absolutely normal without any signs of acute necrotizing enterocolitis.

EXAMPLE 6

Topical Treatment of Skin Ulcers

Ten patients (6 men—4 women) affected by diabetic ulcers of legs, known to be particularly difficult to treat since connected to a systemic disease, were treated twice a day with topical application of 5% aqueous solution of PMF Ab. The complete recovery occurred after 4-6 weeks in seven patients with diabetic ulcers having a surface ranging from 2.5 to 24.5 cm; in three cases, the initial lesion improved to an extent from 60% to 85%.

EXAMPLE 7

Treatment of Oral Lesions

The effectiveness of PMF Ab, either in free form or incorporated in microspheres, was tested in a clinical trial in which 50 patients (males aged between 18 and 43 years, mean age 28.73), free of pathological conditions other than recurrent oral stomatitis were enrolled (No. 25) in Group I of the study (topical application of 5% aqueous solution of PMF Ab, 3 times a day) and in control Group II (rinse with benzidamine hydrochloride 3 times a day for 2 minutes).

The size of the ulcers, pain (with VAS score) and the degree of satisfaction of the treatment have been assessed. Topical application of PMF Ab resulted in complete resolution of ulcers in 8 patients within 2-4 days, 4-7 days in 10 patients, within 7-10 days in the remaining 7 patients in Group I. In the control group II, there was complete healing of aphthous ulcers in 3 patients within 2-4 days, 4-7 days in 9 patients, within 7-10 days in the remaining 10 patients, with 3 patients still suffering from the disease. The average size of ulcers in the two groups was significantly lower from the fourth day for the study group (I) compared to the control group (II).

EXAMPLE 8

Therapy of Corneal Lesions in Dogs

The research was performed on 5 dogs that had photophobia, epiphora, blepharospasm. The dogs had corneal lesions due to generic type trauma (injury by foreign bodies, cat scratch, etc.).

Eye drops containing 5% PMF Ab were administered twice daily by conjunctival instillation for a period of 8-10 days.

Results

Two superficial ulcers, one recurrent indolent ulcer and two deep ulcers were detected in the five dogs under test.

Healing of corneal injury occurred in all subjects. Healing means the complete healing of the lesion and the negativisation of the fluorescein test, as well as the disappearance of symptoms reported at clinical examination (blepharospasm, photophobia, epiphora). In all cases it was also possible to preserve the animals' sight and no permanent cicatritial leukoma was observed notwithstanding that no other treatment (e.g. local corticosteroids) or any other therapeutic agent had been used.

The mean recovery was 6 days. It should be noted that, in addition to healing of the ulcer, probably due to an effect similar to that of limbial stem cells, PMF Ab has also acted as an antibacterial agent, preventing the development of secondary infections, and as anti-inflammatory agent, leading to a complete wound healing without residual scars.

EXAMPLE 9

Treatment of Alopecia

Alopecia can be effectively prevented and treated by PMF Ab, preferably by applying in succession a first topical composition which acts on the hair bulb in the catagen phase and a second topical composition that stimulates the anagen phase of hair re-growth.

The first topical formulation comprises as active ingredients oil resin capsicum, Vitamin PP and caffeine in addition to conventional excipients. The second composition, to be applied on the scalp 15 to 30 minutes after application of the first composition, comprises PMF Ab partially in free form and partially encapsulated in microspheres and other ingredients selected from sericin, Aloe vera extract, caffeine, melatonin and panthenol. Examples of suitable formulations are reported below:

1 Pre-Treatment
Oil resin *capsicum* 0.05%
Vitamin PP 0.20%
Caffeine 0.01%
excipients qs
2 Treatment
P.M.F. Ab 10.00%
P.M.F. Ab micro encapsulated 2.5%
Sericin 1.00%
Aloe 1.00%
Panthenol 0.20%
Melatonin 0.005%
Caffeine 0.01%
excipients qs The formulations were tested clinically on 30 cases of recurrent hair loss (telogen), especially in spring and autumn. The hair loss has been prevented in 88% of males and 75% females.

In 20 patients subjected to chemotherapy (women with breast cancer), only 12% of patients lost their hair, 20% hair have thinned, but did not fall, in all cases with no adverse effect.

The formulations were also tested in 10 patients with sharp loss of hair, 10 patients with chronic loss of hair, 5 patients with alopecia areata, 40 patients with androgenetic alopecia and 7 patients with cicatricial alopecia.

In sharp loss of hair, the response to therapy of patients, 8 women and 2 men, was variable.

After two months of application of the product, once a day, a clear reduction in hair loss was detected in 8 patients (7 women—1 man) with a modest recovery in only one case (male) in the third month of therapy while in remaining two cases (respectively a man and a woman), the situation was unchanged.

In chronic hair loss, of the 10 cases treated (9 women and 1 man) 8 patients had a decrease after two months of therapy. Two patients did not respond to therapy.

In alopecia areata all treated subjects (5 patients, 3 women and 2 men) had little or no response after two months of therapy.

40 subjects (30 men and 10 women) affected by androgenetic alopecia were treated. After two months of therapy, a reduction in hair loss and improvement in the appearance of hair, quantifiable with a larger diameter of the barrel, higher volume and higher gloss of the hair in 30 of the cases treated.

In the other 10 cases, the clinical condition has remained unchanged.

In 7 cases of cicatricial alopecia (4 women and 3 men), in which there was also an inflammatory reaction of the skin with a strong sense of itching, the response was surprising after one month of therapy.

There has been a decline and even disappearance of itching, attenuation of the cutaneous irritative form and a stabilization of the alopecia.

The invention claimed is:

1. A pharmaceutical composition in a topical form of creams, ointments, gels, or lotions; comprising a combination of 0.80-2.90 pg/mg interleukin-1a; 0.02-0.09 pg/mg interleukin-1b; 0.75-5.00 pg/mg interleukin-2; 0.04-0.17 pg/mg interleukin-4; 0.10-1.20 pg/mg interleukin-6; 0.50-2.50 pg/mg interleukin-8; 0.50-3.60 pg/mg interleukin-9; 0.50-2.80 pg/mg interleukin-10; 0.50-2.00 pg/mg interleukin-12; 1.10-4.30 pg/mg interleukin-15; 15.00-150.00 pg/mg interleukin-17; 3.00-30.00 pg/mg interferon-gamma; 15.00-30.00 pg/mg tumor necrosis factor α; 10.00-30.00 pg/mg interleukin-1 receptor agonist; 150.00-300.00 pg/mg transforming growth factor-β; 300.00-800.00 pg/mg insulin-like growth factor-1; 1.00-10.00 pg/mg nerve growth factor; 5.00-100.00 pg/mg platelet-derived growth factor; 4.80-9.40 pg/mg epidermal growth factor; 15.00-50.00 pg/mg bone morphogenetic protein 2; 100.00-200.00 pg/mg fibroblast growth factor basic; 5.00-20.00 pg/mg fibroblast growth factor-2'; 40.00-80.00 pg/mg hepatocyte growth factor; 50.00-300.00 pg/mg vascular endothelial growth factor; 10.00-20.00 pg/mg granulocyte colony-stimulating factor; 100.00-1000.00 pg/mg granulocyte-macrophage colony-stimulating factor; 15.00-50.00 pg/mg leukemia inhibitory factor; 1.00-10.00 pg/mg stem cell factor; 10.00-40.00 pg/mg stromal derived factor-1; 1.00-15.00 pg/mg EOTAXIN-1; EOTAXIN-2; and/or EOTAXIN-3, 1.00-5.00 pg/mg monocyte chemotactic factor-1; 0.50-1.00 µg/mg transferrin; 0.80-2.50 µg/mg lactoferrin; 10.00-40.00 pg/mg lysozyme; 10.00-30.00 µg/mg lactoperoxydase; 0.20-0.70 pg/mg complement C3A; 0.90-2.00 pg/mg complement C4A; 0.20-0.50 mg/mg Immunoglobin G; 0.10-0.20 mg/mg Immunoglobin A; and 0.05-0.15 mg/mg Immunoglobin M.

2. The pharmaceutical composition according to claim 1, wherein the combination is obtained by extraction of colostrum.

3. The pharmaceutical composition according to claim 1, wherein the combination is obtained by extraction of placenta.

4. The pharmaceutical composition according to claim 1, wherein the combination is obtained by extraction of serum collected 5-15 days before partum.

5. The pharmaceutical composition according to claim 1, comprising the combination as the active ingredients in admixture with suitable carriers and/or excipients.

6. The pharmaceutical compositions according to claim 1, further comprising zinc oxide or *Arnica montana* extract.

7. A pharmaceutical composition in an oral form of tablets, comprising a combination of 0.80-2.90 pg/mg interleukin-1a; 0.02-0.09 pg/mg interleukin-1b; 0.75-5.00 pg/mg interleukin-2; 0.04-0.17 pg/mg interleukin-4; 0.10-1.20 pg/mg interleukin-6; 0.50-2.50 pg/mg interleukin-8; 0.50-3.60 pg/mg interleukin-9; 0.50-2.80 pg/mg interleukin-10; 0.50-2.00 pg/mg interleukin-12; 1.10-4.30 pg/mg interleukin-15; 15.00-150.00 pg/mg interleukin-17; 3.00-30.00 pg/mg interferon-gamma; 15.00-30.00 pg/mg tumor necrosis factor α; 10.00-30.00 pg/mg interleukin-1 receptor agonist; 150.00-300.00 pg/mg transforming growth factor-β; 300.00-800.00 pg/mg insulin-like growth factor-1; 1.00-10.00 pg/mg nerve growth factor; 5.00-100.00 pg/mg platelet-derived growth factor; 4.80-9.40 pg/mg epidermal growth factor; 15.00-50.00 pg/mg bone morphogenetic protein 2; 100.00-200.00 pg/mg fibroblast growth factor basic; 5.00-20.00 pg/mg fibroblast growth factor-2'; 40.00-80.00 pg/mg hepatocyte growth factor; 50.00-300.00 pg/mg vascular endothelial growth factor; 10.00-20.00 pg/mg granulocyte colony-stimulating factor; 100.00-1000.00 pg/mg granulocyte-macrophage colony-stimulating factor; 15.00-50.00 pg/mg leukemia inhibitory factor; 1.00-10.00 pg/mg stem cell factor; 10.00-40.00 pg/mg stromal derived factor-1; 1.00-15.00 pg/mg EOTAXIN-1; EOTAXIN-2; and/or EOTAXIN-3, 1.00-5.00 pg/mg monocyte chemotactic factor-1; 0.50-1.00 µg/mg transferrin; 0.80-2.50 µg/mg lactoferrin; 10.00-40.00 µg/mg lysozyme; 10.00-30.00 µg/mg lactoperoxydase; 0.20-0.70 pg/mg complement C3A; 0.90-2.00 pg/mg complement C4A; 0.20-0.50 mg/mg Immunoglobin G; 0.10-0.20 mg/mg Immunoglobin A; and 0.05-0.15 mg/mg Immunoglobin M.

8. The pharmaceutical composition according to claim 1; wherein the combination is obtained by passing through a membrane or a molecular sieve with a cut-off of 300,000 dalton.

* * * * *